United States Patent [19]
Mendelson et al.

[11] Patent Number: 6,084,661
[45] Date of Patent: Jul. 4, 2000

[54] OPTICAL METHOD AND APPARATUS FOR MEASURING CARBON MONOXIDE IN NON-HEMOLYZED BLOOD

[75] Inventors: Yitzhak Mendelson; Karen Mendelson, both of Worcester, Mass.

[73] Assignee: Worcester Polytechnic Institute, Worcester, Mass.

[21] Appl. No.: 09/074,186

[22] Filed: May 7, 1998

Related U.S. Application Data

[60] Provisional application No. 60/045,859, May 8, 1997.

[51] Int. Cl.$^7$ .................................................. G01N 33/48
[52] U.S. Cl. ........................ 356/41; 356/39; 250/343; 250/347; 435/29; 435/4
[58] Field of Search ........................ 356/39, 41; 250/343, 250/347; 435/29, 4

[56] References Cited

U.S. PATENT DOCUMENTS

| | | |
|---|---|---|
| 4,324,556 | 4/1982 | Robertson et al. .................. 23/230 |
| 5,061,632 | 10/1991 | Shepherd et al. .................. 436/66 |
| 5,766,875 | 6/1998 | Hafeman et al. . | |
| 5,810,723 | 9/1998 | Aldrich . | |

FOREIGN PATENT DOCUMENTS

0524083B1  1/1993  European Pat. Off. .

OTHER PUBLICATIONS

M. Cicale, M.D. "The Usefulness of a New Portable Finger Oximeter" (8G Immunologic Mechanism).

Pieralli et al. "Three wavelength optical oxymetry including the measurement of carboxyhemoglobin concentration" 2331:80–88 (1994).

Vreman et al. "Carbon Monoxide in Blood: An Improved Microliter Blood–Sample Collection System with Rapid Analysis by Gas Chromatography" 30(8): 1382–1386 (1984).

*Primary Examiner*—Frank G. Font
*Assistant Examiner*—Roy M. Punnoose
*Attorney, Agent, or Firm*—Hamilton, Brook, Smith & Reynolds, P.C.

[57] ABSTRACT

Carbon Monoxide (CO) is a colorless, tasteless, and odorless gas which causes asphyxiation by combining with a strong affinity to blood hemoglobin. Unless a patient is quickly identified as having CO poisoning, the patient could face severe medical consequences including death.

This patent describes a reagentless optical method for measuring carboxyhemoglobin (HbCO) in a whole undiluted blood sample that can be obtained from a fingerstick. A battery-operated triple wavelength device measures light transmission at frequencies of 548 nm, 810 nm and 950 nm through a 40 $\mu$L sample of undiluted whole blood placed in standard disposable glass capillary tube. Having a portable point-of-care device, for uses by paramedics during an emergency situation, in the emergency room, or in a physician's office, can provide accurate immediate confirmation of CO poisoning.

23 Claims, 7 Drawing Sheets

OPTICAL METHOD AND APPARATUS FOR MEASURING CARBON MONOXIDE IN NON-HEMOLYZED BLOOD

RELATED APPLICATION(S)

This application claims priority to Provisional Application Number 60/045,859 filed May 8, 1997 entitled "Optical Method and Apparatus for Measuring Carbon Monoxide in Non-hemolyzed Blood", the entire teachings of which are incorporated herein by reference.

BACKGROUND OF THE INVENTION

Carbon monoxide (CO) is a colorless, tasteless, and odorless by-product gas that results from exogenous sources such as pollution, fires, or smoking. In the blood, CO combines readily with hemoglobin (Hb) in a reversible chemical reaction to produce carboxyhemoglobin (HbCO). Headaches, dizziness, nausea and other flu-like symptoms are often associated with HbCO levels around 10–15%. With higher HbCO levels between 15% and 40%, common symptoms include severe headaches, mental confusion, and fainting. When the HbCO levels in blood exceed 40%, unconsciousness or death may result.

Traditionally, HbCO has been measured by automated clinical analyzers in the laboratory. One common clinical analyzer is the IL-482 CO-Oximeter (manufactured by Instrumentation Laboratories, Lexington, Mass.). This oximeter is an automated instrument which analyzes a blood sample for total hemoglobin (THb), percent oxyhemoglobin (%HbO$_2$), %HbCO, and reduced hemoglobin (%RHb) contents. (Brown L., "A New Instrument for the Simultaneous Measurement of Total Hemoglobin, % Oxyhemoglobin, % Carboxyhemoglobin, % Methemoglobin, and Oxygen Content in Whole Blood" *Institute of Electrical and Electronic Engineering* (IEEE) *Transactions on Biomedical Engineering*, 27:132–8(1980); and Instrumentation Laboratory, IL-482 CO-Oximeter Operator's Manual, Lexington, Mass.) Clinical analyzers, such as the IL-482, are best operated in a well equipped laboratory by highly trained personnel. These analyzers are usually used in a hospital setting because they are bulky, expensive, and powered by 110 V a.c. In addition, CO-Oximeters require a hemolyzed blood sample for analysis. For the reasons mentioned above, these clinical analyzers are not suitable for use by paramedics in the field.

Although several types of devices are currently available for detecting CO levels in ambient air, the definitive diagnosis of CO poisoning is made in the hospital by measuring HbCO levels in blood utilizing spectrophotometric means. HbCO and HbO$_2$ both absorb less light in the red region of the spectrum (i.e. ~660 nm) than RHb. Therefore, blood that contains elevated levels of CO possesses the same distinctive red color as blood that is highly oxygenated. For this reason, based on color alone, it is difficult to differentiate well oxygenated blood from blood containing high levels of CO.

Recently, non-invasive pulse oximeters for measuring arterial oxygen saturation (SaO$_2$) in blood have become widely available. These pulse oximeters are popular devices for use by paramedics for rapid assessment of the oxygenation status of a patient. Although pulse oximeters can accurately measure SaO$_2$, they do not provide direct measurements of HbCO levels in blood. In fact, in the presence of elevated levels of >10% HbCO, pulse oximeters produce false readings since HbCO and HbO$_2$ have similar optical absorption properties. (Mendelson Y., "Pulse Oximetry: Theory and Applications for Noninvasive Monitoring", *Clin Chem*;38(9) : 1601–7(1992))

SUMMARY OF THE INVENTION

In accordance with the invention a compact microspectrophotometer for measuring HbCO in a sample of whole undiluted blood is provided. This device has several advantages over current clinical analyzers because it is battery-operated, inexpensive, eliminates the need to hemolyze the blood sample, and is small. Therefore, it is particularly suitable for use by paramedics in the field to provide accurate immediate confirmation of CO poisoning. An additional benefit of this device is in patient-side testing during prolonged monitoring of HbCO levels in patients undergoing hyperbaric oxygen treatment for CO poisoning.

To accomplish the foregoing, a portable invasive system/method for measuring/detecting the carbon monoxide level in non-hemolyzed whole blood sample taken from a patient is provided. The system/method comprises subjecting the sample to radiation at least three different wavelengths $\lambda_1$, $\lambda_2$, $\lambda_3$; determining the absorption of the blood at each wavelength and using the determination at $\lambda_1$ to select one of several calibration curves relating to the blood hemotocrit of the patient. Then, using the selected calibration curve, computing the carbon monoxide level in the patient. In a preferred embodiment the wavelengths $\lambda_1$, $\lambda_2$, $\lambda_3$ are about 548 nm, 810 nm and 950 nm, respectively, and the absorption at each wavelength is determined substantially simultaneously using light emitting diodes or diode lasers operable at the foregoing wavelengths.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
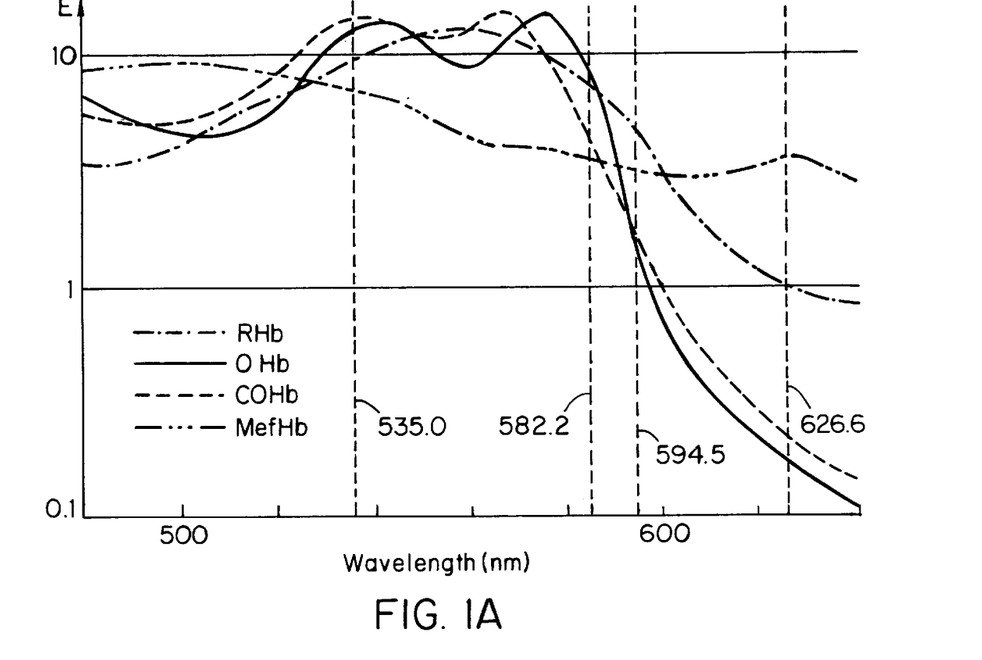
FIG. 1A is a plot of the optical absorbance spectra of Hb, HbO$_2$, MetHb, and HbCO in the visible wavelength region.
Figure 1B:
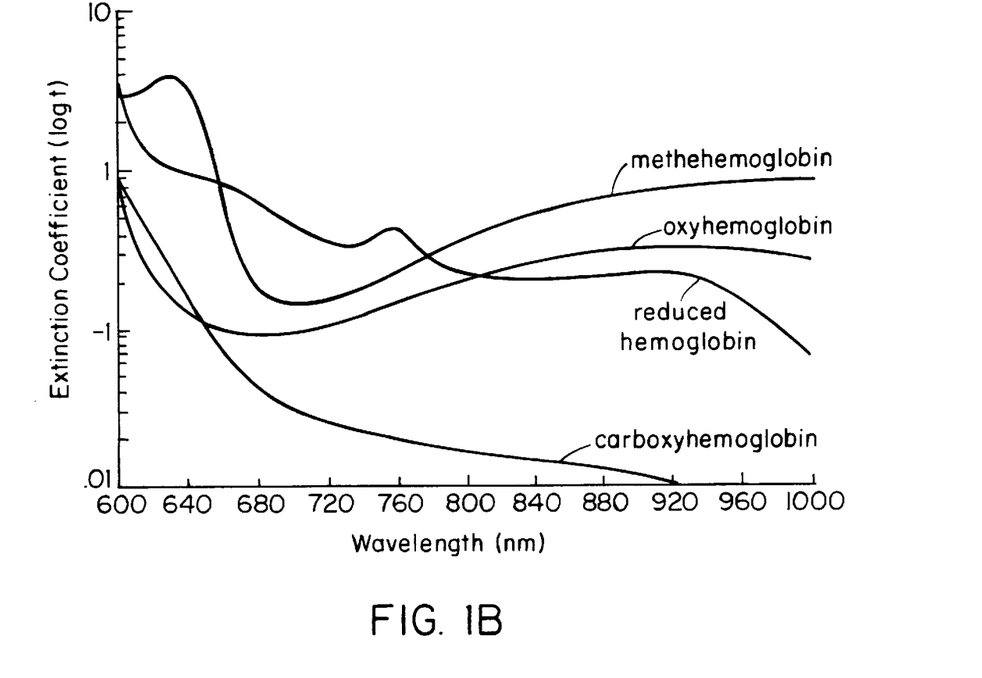
FIG. 1B is a plot of the optical absorbance spectra of Hb, HbO$_2$, MetHb, and HbCO in the visible near-infrared region.

Spectrophotometric measurements in blood rely on the difference in the optical extinction or absorption coefficient of different hemoglobin derivatives, as illustrated in the plot of FIG. 1. Traditionally, CO-Oximeters, such as the IL-482, measure the absorption of hemolyzed blood using four specific wavelengths in the visible region of the optical spectrum at 535.0 nm, 585.2 nm, 594.5 nm, and 626.6 nm. The concentrations of reduced hemoglobin Rhb, oxyhemoglobin $HbO_2$, carboxyhemoglobin HbCO and methahemoglobin MetHb are then determined by solving four independent equations derived from Beer-Lambert's Law. These results are expressed as a percentage of the total hemoglobin THb in a given sample of blood.

In selecting suitable excitation wavelengths for the measurement of HbCO in the device of the present invention, initially two wavelengths specific to the green region of the spectrum at 548 nm and 568 nm, as shown in FIG. 1A were considered. The 548 nm wavelength is an isobestic point (a wavelength at which the optical extinction coefficients are the same for two or more hemoglobin derivatives). At this specific reference wavelength, the extinction coefficients of RHb, $HbO_2$ and HbCO are nearly equal. The 568 nm wavelength was considered for two reasons; first, because it is highly dependent on variations in HbCO, and second, because it is advisable to work at the maxima of the optical absorption spectrum in order to eliminate the sensitivity due to wavelength shifts.

From a practical point, however, selecting 548 nm and 568 nm wavelengths posed several technical problems. First, the use of undiluted whole blood, rather than hemolyzed blood, resulted in reduced light transmission due to multiple scattering by the red blood cells (RBCs). Second, the use of a standard capillary tube with an inner diameter of 1.2 mm as an optical cuvette (compared to a 0.1 mm thick cuvette used in bench top CO-Oximeters, such as the IL-482) resulted in large absorption and thus reduced sensitivity to small changes in HbCO. Third, the optical properties of the different hemoglobin derivatives in the visible region of the spectrum require the use of very narrow bandpass filters which would raise the overall cost of the device. Therefore, for the reasons outlined above, using wavelengths in the green region of the spectrum proved unsuitable for accurately detecting small differences in the concentration of HbCO in a sample of whole (undiluted) blood.

To overcome these limitations, two wavelengths from the near-infrared region of the spectrum (see FIG. 1B) were ultimately selected; first, because the extinction coefficient of HbCO is about 500 times smaller in this region compared to the green region of the spectrum and second, because the scattering of light is inversely proportional to the fourth power of the wavelength used. (Van de Hulst HC, "Light Scattering by Small Particles" New York: Dover Publications Inc. (1981)) Accordingly, one wavelength was chosen around 810 nm which coincides with the isobestic point of RHb and $HbO_2$. At this wavelength, the absorption of blood is dependent both on HbCO and on THb. Since there is no single wavelength that is isobestic for RHb, $HbO_2$ and HbCO in the near-infrared region of the spectrum, the second wavelength is selected around 950 nm. At this wavelength, the extinction coefficient of blood is both minimally dependent upon HbCO and the difference between the extinction coefficients of $HbO_2$ and RHb is the smallest for the wavelength regions where the absorption of HbCO is minimal. Note, however, that in selecting wavelengths in the 800–1000 nm region of the optical spectrum, one has to assume that the concentration of MetHb in the sample of blood is negligible.

A third wavelength of 548 nm was also selected as a result of experimental data, as will be described below, to determine which of several possible calibration curves to select to compensate for differences in measurements caused by different THb levels from one patient to another.

Figure 2:
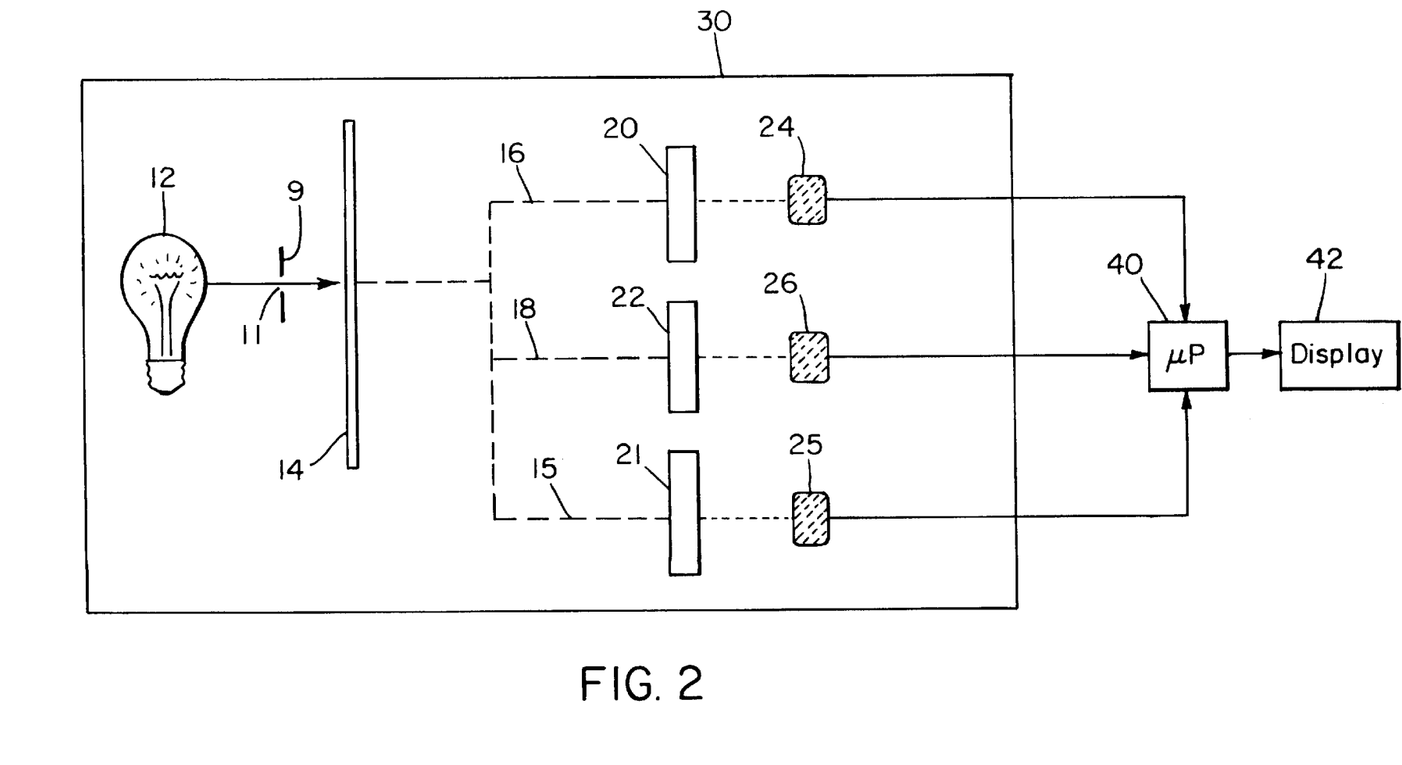
FIG. 2 is a schematic diagram of a first preferred embodiment of the invention.

FIG. 2 illustrates the optical layout of a first embodiment of a microspectrophotometer 10 of the invention. The device consists of a small light source 12, a capillary tube 14, a set of optical fibers 15, 16 and 18, three interference filters 20, 21, 22, three photodetectors 24, 25, 26, microprocessor 40 and display 42. The lamp, optical fibers, filters, and photodetectors are mounted inside an opaque black housing 30 (optional dimensions: 6 mm×40 mm×48 mm). Light, preferably from a 0.3W prefocused miniature flashlight lamp 12, powered by a 1.5 V battery (not shown), is focused through a horizontal hole 11 (about 1.0 mm diameter) onto the glass capillary tube 14. The capillary tube is used as an inexpensive widely available optical cuvette. The capillary tube is filled with a 40 μL sample of whole blood taken from a patient by a finger stick. One end of the tube 14 is sealed and then inserted in a vertical position into the housing 10 adjacent the slit 9. Three sets of optical fibers 15, 16 and 18 are used to conduct the light transmitted through the blood filled capillary tube to three optical bandpass filters 20, 22, and 21 with peak emission wavelengths of 810 nm, 950 nm and 548 nm, respectively (bandwidth: ~9.25 nm).

Mounted behind each filter is a respective photodiode 24, 25, and 26 (such as a Burr-Brown OPT 301 photodiode with an integrated amplifier chip). Preferably, the silicon photodiode chip (active area: 2.29 mm×2.29 mm) is combined with a transimpedance amplifier in a single package which eliminates noise pick-up due to stray capacitance. A combination of internal and external feedback resistors (not shown) are used to set the gain of the transimpedance amplifier. The respective output voltages from each photodiode are connected directly to microprocessor 40.

The first measurement is performed at 548 nm to determine hemoglobin content (Hb) or hematocrit (Hct) of the non-hemolyzed blood sample in the tube 14. Based on the absorption at 548 nm, the instrument uses a working or calibration curve stored in microprocessor 40 to determine Hb or Hct.

Figure 7:
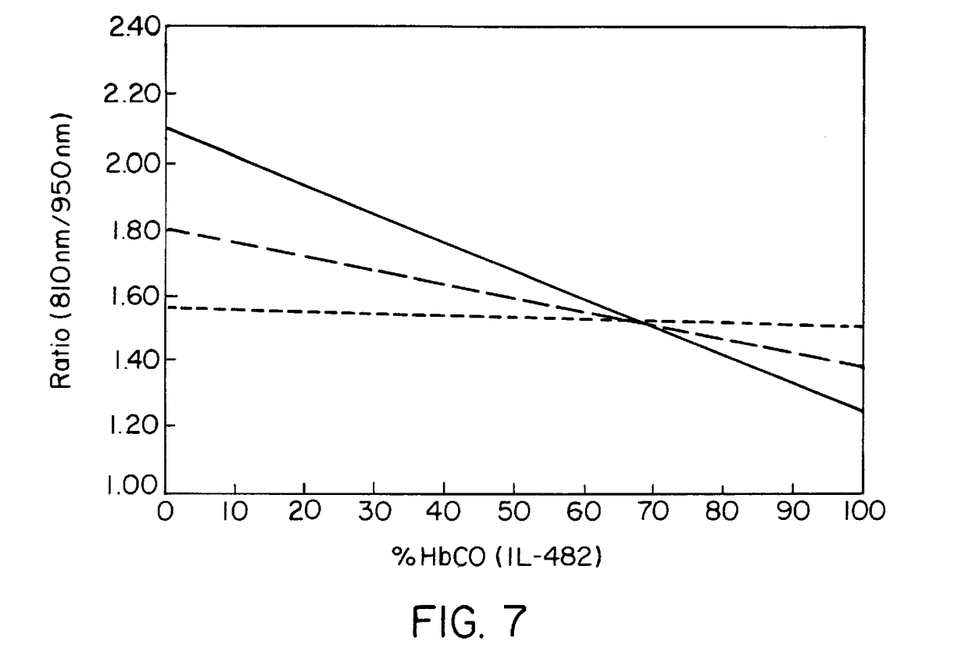
FIG. 7 is a comparison plot of light transmission ratio (810 nm/950 nm) and %HbCO for three distinct THb levels. Solid line: THb=15.3 g/dL, dashed line: THb=9.8 g/dL dotted line: THb=4.7 g/dL.

The relationship between light absorption ratio (810/950 nm) and known HbCO for three different levels of total hemoglobin (THb) is shown in FIG. 7. Either THb or Hct is sufficient. In reality, patients could have different THb levels from the three specific examples shown on this figure. Therefore, additional calibration lines should be generated a priori for a wider range of THb covering for example incremental changes every 0.2 g/dL. Although the exact incremental change number is not critical, it must be small enough to assure accurate clinical diagnosis.

From these additional calibration curves, the appropriate statistical regression coefficients (slope and y-intercept if these equations represent a straight line or additional coefficients if the calibration curves deviate from a linear relationship) can be derived for each calibration curve. For example, if 5 different calibration curves all follow a straight line relationship, i.e. $y=a_0+a_1x$, 5 slopes (i.e. five different $a_o$ values) and 5 different y-intercept (i.e. $a_1$) coefficients can be obtained from each curve (Note that only 2 coefficients per line are required to reconstruct a straight line). From these regression coefficients, a graph relating the known Hct or Hb versus the value of that coefficient can be constructed. However, these relationships result in a $3^{rd}$ degree polynomial of the form $y=a_0+a_1x+a_2x^2$, an additional graph is needed to relate $a_2$ to Hct or Hb.

From the actual data points in the graphs two (or more, depending on the general shape of the relationships) new regression relationships can be created to estimate the specific regression coefficients (i.e. the "a" coefficients) for any value of Hb or Hat which is determined from the light absorption measured at 548 nm.

Once the specific coefficients that correspond to the estimated Hb values are known, they are stored in the memory of microprocessor 40 for subsequent determination of HbCO. For example, for a Hb value of 4.7 g/dL, $a_0=1.567$ and $a_1=-0.001$, the relationship HbCO=1.567−0.001·Ratio (810/950) can be used to display on display 42 the unknown HbCO after the Ratio(810/950) is determined independently.

Through extensive blood experimentation shown in FIG. 7, we found unexpectedly that the three calibration curves all intersect at a single "pivoting" point around a HbCO value of about 68% and a 810/950 ratio of about 1.56. Therefore, each calibration curve shown in FIG. 7, including additional calibration curves for other values of THb not shown in FIG. 7 provided they also intersect at the same pivoting points, could be uniquely defined using only a single "a" coefficient which describes either the slope or y-intercept of that calibration line. This would further simplify the operation of the device by reducing the number of regression coefficients that are needed to compute %HbCO.

Note that, in principle, since total Hb (or Hct) must be determined before HbCO can be calculated, the device has the capability to display both Hb (or Hct) and HbCO. This offers an additional commercial advantage to the present invention.

In-Vitro Blood Experimentation

Experiments were conducted to assess the sensitivity and test the linearity of a prototype spectrophotometer of the invention for changes in blood HbCO levels. Whole undiluted cow blood obtained from a local slaughter house was heparinized and filtered to remove solid debris. A 10 cc sample of blood (Hct=42%) was transferred into a syringe and gently mixed with pure $O_2$ gas to raise the $HbO_2$ level to ~100%. To alter the HbCO in the blood, a mixture of 5.4% $CO_2$-balanced gas was gradually introduced into the syringe and gently mixed with the blood in a stepwise manner. Each time the concentration of CO gas in the syringe was raised, a standard glass microhematocrit capillary tube was filled with blood and both ends of the capillary tube were sealed with a cap of Critoseal™. Simultaneously, the blood in the syringe was analyzed in duplicate to determine the %HbCO using an IL-482 CO-Oximeter as a reference. A total of 16 capillary tubes were prepared in this way for analysis by the microspectrophotometer 10. Photometric measurements were made shortly after the capillary tubes were filled to minimize significant sedimentation of the RBCs. Each measurement was repeated 3 times and the results were averaged. All measurements were performed at room temperature.

Figure 3:
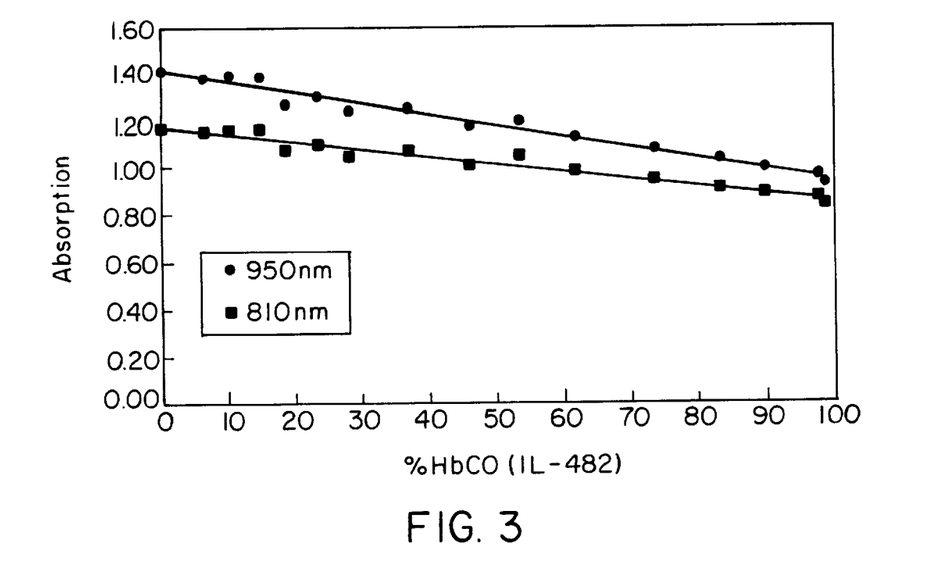
FIG. 3 is a plot of absorption as a function of known %HbCO. Hct=42% (THb=12.9 g/dL). Regression equation for $\lambda$=810 nm: y=−0.0033x+1.18; $R^2$=0.959. Regression equation for $\lambda$=950 nm: y=−0.0047x+1.41; $R^2$=0.976. Each line was fit by linear regression.

The absorption by the blood-filled capillary tubes measured at 810 nm and 950 nm versus the concentration of HbCO as measured by the IL-482 CO-Oximeter is shown in FIG. 3. Regression analysis of the data shown in FIG. 3 revealed that the relationship followed quite closely a linear trend for both wavelengths. Despite light scattering by whole blood, surprisingly, this relationship appears to obey Beer-Lambert's Law which is commonly used for spectrophotometric analysis of hemolyzed blood samples illuminated by collimated monochromatic light. One possible explanation for this linear trend could be due to the relatively short optical pathlength through the blood-filled capillary tube thus limiting considerably the amount of light scattering by the RBCs.

Figure 4:
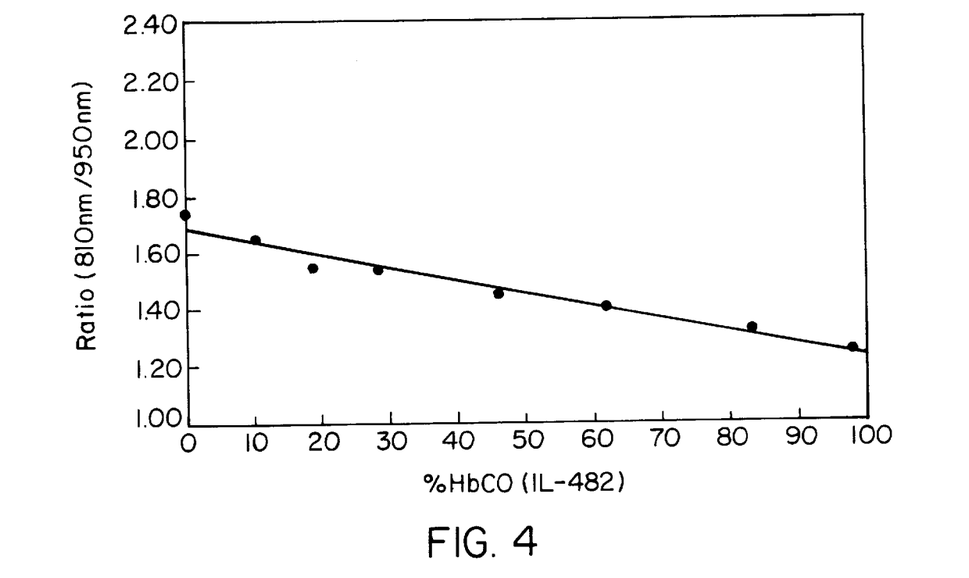
FIG. 4 is a plot of transmission ratio (810 nm/950 nm) as a function of %HbCO for THb of 12.9 g/dL (Hct=42%). Regression equation: y=−0.0046x+1.688; $R^2$=0.961.
Figure 5:
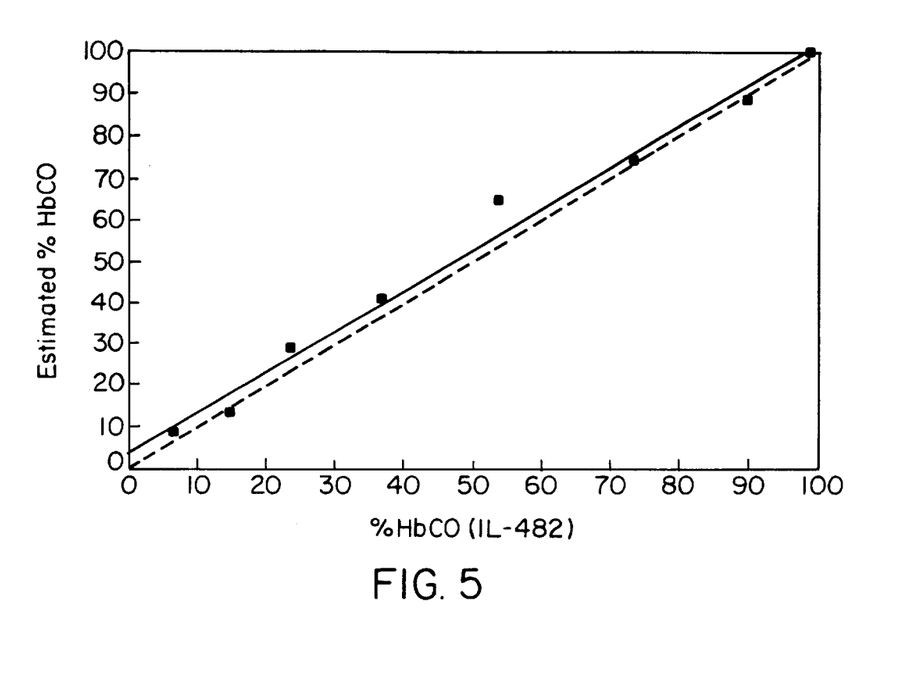
FIG. 5 is a plot of estimated vs. known %HbCO for THb of 12.9 g/dL (Hct=42%). Regression equation: y=0.98x+3.79; $R^2$=0.986; Error=4.45%. Solid line describes the linear regression line through the data. Ideal (dashed line) relationship is shown for comparison.

Next, 8 out of 16 blood-filled capillary tubes were randomly selected and used to construct a calibration curve (shown in FIG. 4) which relates the quantitative changes in the 810 nm/950 nm ratio to the percent HbCO measured by the IL-482 CO-Oximeter reference. This calibration curve was then used to estimate independently the %HbCO from the remaining 8 blood samples. Results from this regression analysis are shown in FIG. 5. In comparison to the IL-482 clinical analyzer, measurements obtained with the prototype spectrophotometer had an average error of ~4.45%. Although clinical analyzers provide more accurate results, it is believed that this initial accuracy would certainly be sufficient for paramedics who often need a quick, simple and robust method to confirm if a patient is suffering from CO poisoning.

Figure 6A:
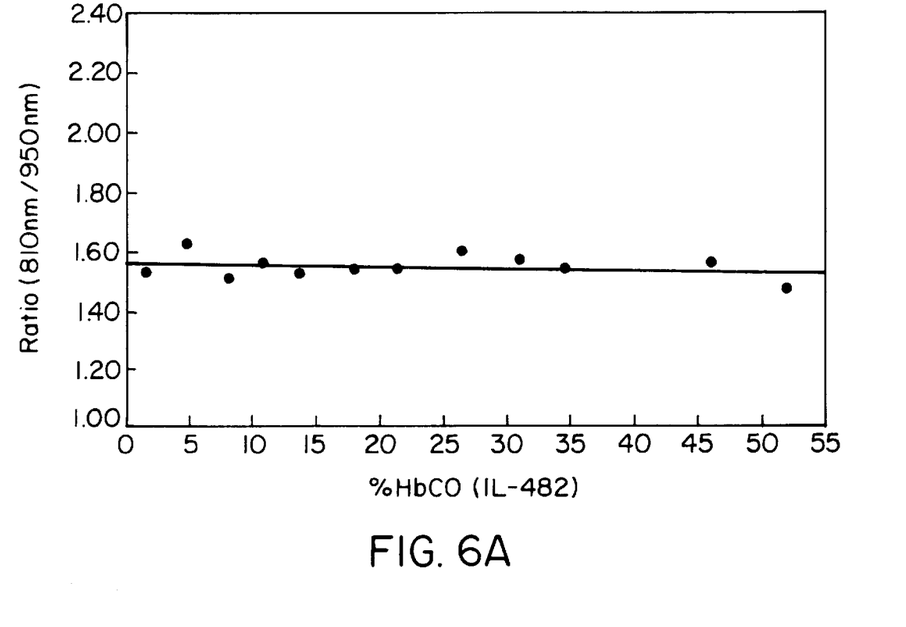
FIG. 6A is a plot of transmission ratio (810 nm/950 nm) as a function of %HbCO for a THb of 4.7 g/dL (Hct=18%), regression equation: y=−0.001x+1.567; $R^2$=0.072.
Figure 6B:
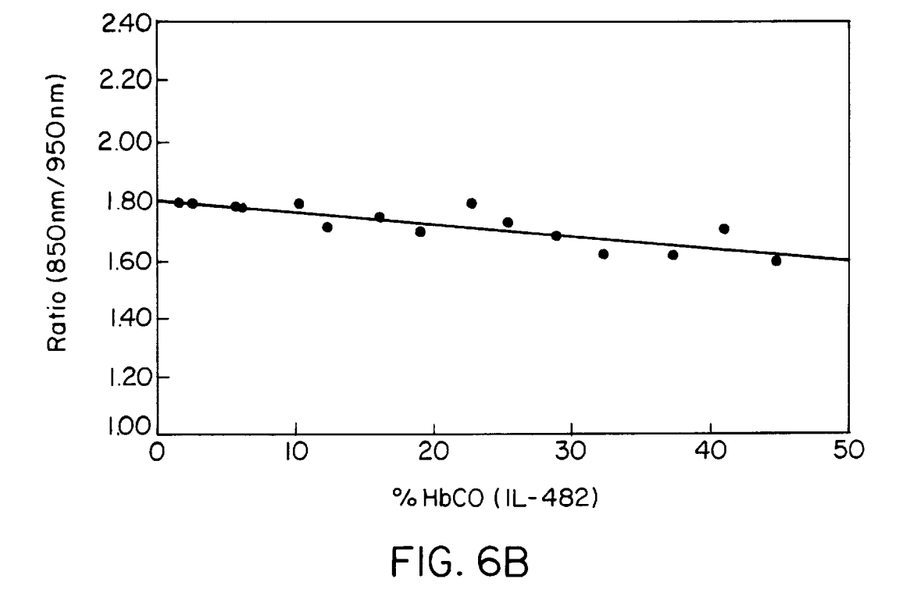
FIG. 6B is a plot of transmission ratio (810 nm/950 nm) as a function of %HbCO for a THb of 9.8 g/dL (Hct=38%), regression equation: y=−0.004x+1.807; $R^2$=0.0730.
Figure 6C:
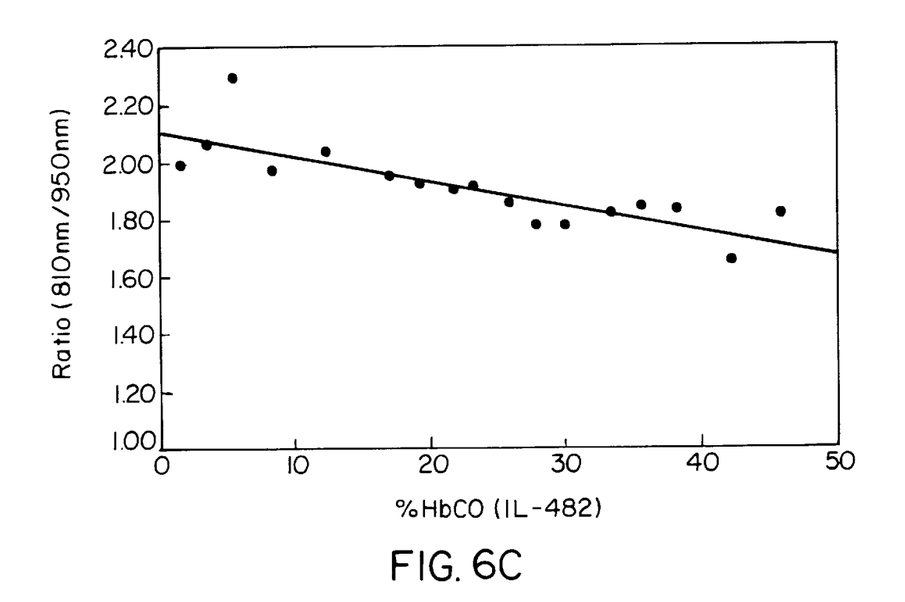
FIG. 6C is a plot of transmission ratio (810 nm/950 nm) as a function of %HbCO for a THb of 15.3 g/dL (Hct=63%), regression equation: y=−0.009x+2.100; $R^2$=0.680.

In another set of experiments, the dependency of the absorption ratio measured at 810 and 950 nm on THb was investigated. To perform these experiments, a blood sample was centrifuged and then the RBCs and plasma were remixed in various proportions to obtain Hematocrit Hct levels of three widely varying concentrations of ~18% (typical for an anemic person), ~38% (representing a healthy individual), and ~63% (typical for a polycythemic patient). For each Hct level, a separate syringe was filled with 15 cc of blood and gradually the concentration of HbCO was altered between 0 and ~50% as described above. Results of these experiments are summarized in FIGS. 6A–C. The linear regression lines for each data set shown in FIGS. 6A–C were then combined in FIG. 7 yielding three distinct calibration curves to show the dependence of the 810 nm/950 nm absorption ratio on Hct for different levels of HbCO. Note that all three regression lines were extrapolated theoretically above the highest level of HbCO shown in FIGS. 6A–C to span the entire range between 0 and 100%. From the three representative lines shown in FIG. 7, it is evident that to measure %HbCO accurately in whole undiluted blood, instead of using a single universal calibration curve, the appropriate calibration lines should be used to correct for changes in THb.

Figure 8:
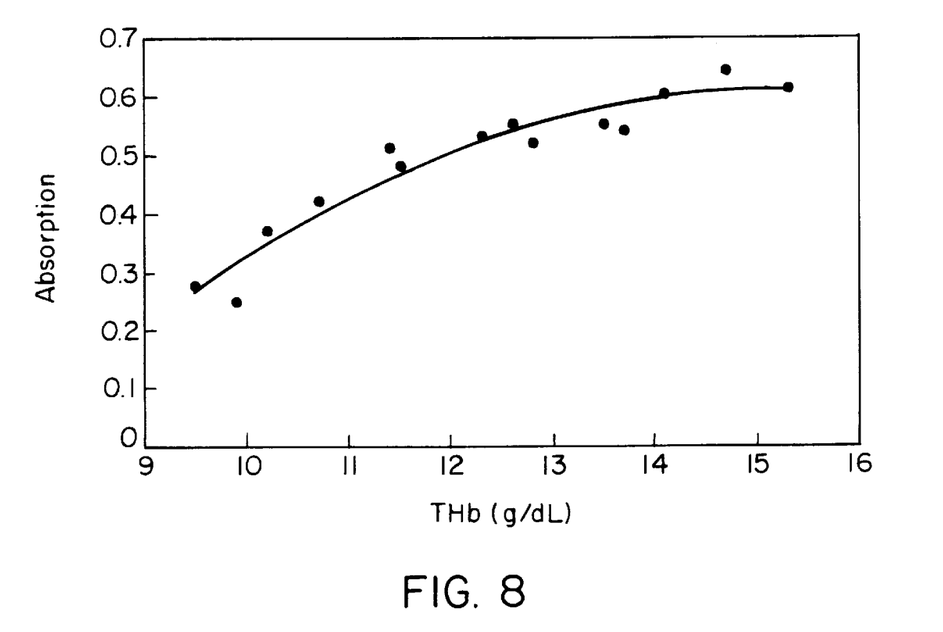
FIG. 8 is a plot of optical absorption at λ=548 nm as a function of THb for blood with HbCO <1%. Regression equation: $y=0.01x^3-0.25x^2+2.79x-10.75$; $R^2$=0.97.

As shown in FIG. 7, a given absorption ratio could result from different concentrations of THb. Therefore, the most practical way to determine the dependence of the calibration curve on THb is to construct a separate calibration curve that describes the relationship between the optical absorption properties of blood and THb for any value of HbCO. To obtain this unique relationship, a new series of experiments were conducted in which one of the optical filters in the prototype device was temporarily replaced with an isobestic wavelength of 548 nm and the absorption of 14 new blood samples was measured with THb levels ranging between 9–16 g/dL. As shown in FIG. 1A the optical absorption of blood at this wavelength is independent of HbCO and is strongly dependent on THb. As expected, the data, which is shown in FIG. 8, revealed that the light absorption rose monotonically as THb is increased. Therefore, in a preferred embodiment of this invention, three wavelengths (e.g. 548, 810 and 950 nm) are used to measure light absorption in a blood sample simultaneously. One wavelength 548 nm is used to determine THb (or blood Hematocrit). The other two wavelengths are used to select the correct calibration curves and compute the unknown level of HbCO in the sample. A simple microprocessor with built-in analog-to-digital converter capabilities can be used to perform these measurements automatically and display both the THb (or Hematocrit) of the blood and the unknown HbCO on one or two different digital meters.

HbCO levels in blood are a useful test for clinically-significant CO exposure because they can be easily measured. The method and apparatus of the present invention represents a new, cost effective option to quickly measure CO in blood during emergency situations. The use of whole blood obtained directly from a finger-prick has a major advantage since it is easy to collect and does not require complicated or costly procedures normally employed to hemolyze the blood in bench-top clinical analyzers. Once the measurement is complete, the sample, which is contained inside a capillary tube, can be safely disposed. The entire measurement should take less than 2 minutes after obtaining blood from a patient.

The major advantages of the present invention are that: (1) no chemical reactions are required, (2) results can be obtained instantaneously once the blood-filled capillary tube is placed in the device, (3) it is light weight, compact, and portable; therefore, the device can be used in various settings such as in ambulances, blood donation centers, or accident sites, (4) sample size is small (<40 $\mu$l), and (5) regular maintenance is not required. Despite these advantages, one of the apparent limitations is the dependence of the calibration curves on Hct or THb concentrations thus precluding the possibility of using a single calibration curve to derive the concentration of HbCO in blood. Therefore, presently, for greatest accuracy the final measurement requires a two-step process; first, the determination of THb, using the 548 nm filter and second, using this information, selecting the proper calibration curve to relate the 810 nm/950 nm transmission ratio to HbCO. Despite the satisfactory agreement between the prototype experimental device and HbCO measured by the IL-482 CO-Oximeter, there are other potential sources of error, such as variations in the concentration of MetHb and $O_2$ in the blood. Nevertheless, based on the near infrared optical absorption spectra of blood shown in FIG. 1B, it is expected that these errors would be minimal for patients with otherwise normal physiological levels of MetHb and $O_2$.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

Figure 9:
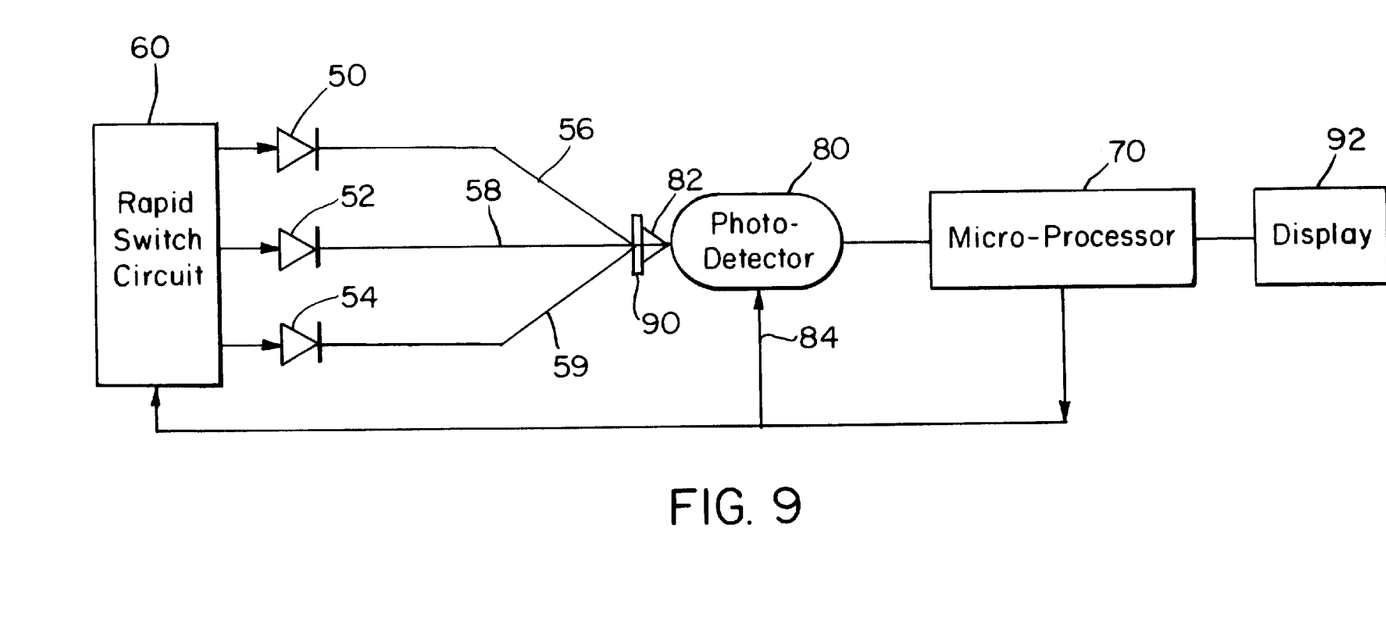
FIG. 9 is a schematic diagram of an alternate preferred embodiment of the invention.

For example, while the invention, as thus far described in connection with FIG. 2 employs a single lightsource and three separate filters and detectors, an alternate embodiment, as shown in FIG. 9 can be employed which reduces costs and parts.

In the embodiment of FIG. 9, three single frequency laser diodes or LED 50, 52 and 54 operating at $\lambda_1$, $\lambda_2$, $\lambda_3$ are successively switched into operation by switching circuit 60 controlled by microprocessor 70. Preferably, each laser diode or LED emits light at the previously noted respective wavelengths of 548 nm, 810 nm and 950 nm, respectively. Light from each laser diode or LED is coupled via optical fibers 56, 58 and 59 to cuvette 90. Light passing through cuvette 90 is partially absorbed in proportion to the degree of CO in the whole blood sample within the cuvette and the wavelength of the input light. The light at each wavelength is coupled to an input port of photodetector 80 where it is successively detected by photodetector 80 and converted to an electrical signal proportional thereto which is coupled to microprocessor 70 where it may by further processed to enhance signal to noise ratio and other well known enhancements.

Microprocessor 70 has stored in memory (not shown) therein the results of previous testing for different levels of Hb or Hct such that once the results of the measurement at 548 nm are known, the appropriate calibration curve is selected by the processor 70 and used to calculate HbCO percentage which is then displayed on display 92 along with Hb or Hct.

Note that the term "about" as used herein in connection with the wavelengths specified is generally meant to cover a range of plus or minus 10 nanometers, although it is more preferable in the case of the 548 nm measurement to stay within a range of plus or minus 5 nanometers and it is preferred that the 950 nm wavelength be maintained no less than 950 nm but it may extend above 950 nm up to 1000 nm. Also, note that the term "Laser(s)" as used in the claims encompasses any type of device, such as, laser diodes or LED's, capable of generating optical radiation at the specified frequencies.

What is claimed is:

1. A system for detecting the presence of carbon monoxide in a blood sample taken from a patient comprising:

apparatus for subjecting the sample to radiation at three wavelengths $\lambda_1$, $\lambda_2$, $\lambda_3$;

one or more photodetectors for determining the absorption of the blood at each wavelength;

a processor for using the determination at a selected one of said wavelengths to select one of several calibration curves relating to the blood hemotocrit of the patient; and using the selected calibration curve, determining the carbon monoxide level in the patient.

2. The system of claim 1, wherein the wavelengths $\lambda_1$, $\lambda_2$, $\lambda_3$ are about 548 nm, 810 nm and 950 nm, respectively, and the absorption at each wavelength is determined substantially simultaneously.

3. The system of claim 1 wherein the blood sample is non-hemolyzed.

4. The system of claim 1 wherein three separate lasers are used to provide the three wavelengths.

5. The system of claim 1 wherein a single photodetector is used to determine absorption at each wavelength.

6. The system of claim 1 wherein a source of white light and three separate filters are used to generate the three wavelengths.

7. A battery powered portable system for measuring the percentage carbon monoxide level in a non-hemolyzed whole blood sample taken from a patient comprising:

at least three lasers for subjecting the sample to radiation at three wavelengths $\lambda_1, \lambda_2, \lambda_3$ wherein $\lambda_1$ is about 548 nm, $\lambda_2$ is about 810 nm and $\lambda_3$ is about 950 nm;

a photodetector for determining the absorption of the blood at each wavelength by detecting the optical radiation after passage through or reflection from the sample at each wavelength and converting the detected optical radiation to an electrical signal proportional thereto;

a processor for using the determination at $\lambda_1$ to select one of several calibration curves relating to the blood hemotocrit of the patient; and for using the ratio of the determination at $\lambda_2$ and $\lambda_3$ to compute the carbon monoxide level in the patient using the selected curve.

8. The system of claim 7 wherein the processor switches on each successive laser to irradiate the sample and a display for displaying the results of the computed CO level in the sample.

9. The system of claim 1 wherein the wavelength $\lambda_1$ is a wavelength at which the absorption of whole blood is independent of HbCO and is strongly dependent on THb; the wavelength $\lambda_2$, is strongly dependent on HbCO and coincides with the isobestic point RHb and $HbO_2$; and the wavelength $\lambda_3$ is minimally dependent on HbCO.

10. The system of claim 9 wherein $\lambda_1$=548 nm, $\lambda_2$=810 nm, $\lambda_3$=950 nm.

11. A method for detecting the presence of carbon monoxide in a blood sample taken from a patient comprising the steps of:

subjecting the sample to radiation at three wavelengths $\lambda_1, \lambda_2, \lambda_3$;

determining the absorption of the blood at each wavelength;

using the determination at a selected one of said wavelengths to select one of several calibration curves relating to the blood hemotocrit of the patient; and using the selected calibration curve, determining the carbon monoxide level in the patient.

12. The method of claim 11, wherein the wavelengths $\lambda_1, \lambda_2, \lambda_3$ are about 548 nm, 810 nm and 950 nm, respectively, and the absorption at each wavelength is determined substantially simultaneously.

13. The method of claim 11 wherein the blood sample is non-hemolyzed.

14. The method of claim 11 wherein three separate lasers are used to provide the three wavelengths.

15. The method of claim 11 wherein a single photodetector is used to determine absorption at each wavelength.

16. The method of claim 11 wherein a source of white light and three separate filters are used to generate the three wavelengths.

17. A method for measuring the percentage carbon monoxide level in a non-hemolyzed whole blood sample taken from a patient comprising the steps of:

subjecting the sample to radiation at three wavelengths $\lambda_1, \lambda_2, \lambda_3$ wherein $\lambda_1$, is about 548 nm, $\lambda_2$ is about 810 nm and $\lambda_3$ is about 950 nm;

determining the absorption of the blood at each wavelength by detecting the optical radiation after passage through or reflection from the sample at each wavelength and converting the detected optical radiation to an electrical signal proportional thereto;

using the determination at $\lambda_1$, to select one of several calibration curves relating to the blood hematocrit of the patient; and using the ratio of the determination at $\lambda_2$ and $\lambda_3$ to compute the carbon monoxide level in the patient using the selected curve.

18. The method of claim 17 including displaying the results of the computed CO level in the sample along with the hematocrit of the patient.

19. The method of claim 11 wherein the wavelength $\lambda_1$, is a wavelength at which the absorption of whole blood is independent of HbCO and is strongly dependent on THb; the wavelength $\lambda_2$, is strongly dependent on HbCO and coincides with the isobestic point RHb and $HbO_2$; and the wavelength $\lambda_3$ is minimally dependent on HbCO.

20. The method of claim 19 wherein $\lambda_1$=548 nm, $\lambda_2$=810 nm $\lambda_3$=950 nm.

21. The system of claim 1 wherein the sample is provided in a capillary tube.

22. The system of claim 7 wherein the sample is provided in a capillary tube.

23. The method of claim 11 wherein the sample is provided in a capillary tube.

* * * * *

UNITED STATES PATENT AND TRADEMARK OFFICE
CERTIFICATE OF CORRECTION

PATENT NO.    : 6,084,661
DATED         : July 4, 2000
INVENTOR(S)   : Yitzhak Mendelson and Karen Mendelson

It is certified that error appears in the above-identified patent and that said Letters Patent is hereby corrected as shown below:

<u>Column 9,</u>
Lines 25 and 26, Claim 10 should read:
-- The system of claim 9 wherein $\lambda_1 \cong 548nm$, $\lambda_2 \cong 810nm$, $\lambda_3 \cong 950nm$. --; and <u>Column 10,</u>
Lines 36 and 37, Claim 20 should read:
-- The method of claim 19 wherein $\lambda_1 \cong 548nm$, $\lambda_2 \cong 810nm$, $\lambda_3 \cong 950nm$. --

Signed and Sealed this

Eleventh Day of March, 2003

JAMES E. ROGAN
*Director of the United States Patent and Trademark Office*